United States Patent
Uchida et al.

(10) Patent No.: US 10,039,861 B2
(45) Date of Patent: Aug. 7, 2018

(54) METHOD FOR PRODUCING ARTIFICIAL RETINA

(71) Applicant: NATIONAL UNIVERSITY CORPORATION OKAYAMA UNIVERSITY, Okayama-shi, Okayama (JP)

(72) Inventors: Tetsuya Uchida, Okayama (JP); Toshihiko Matsuo, Okayama (JP)

(73) Assignee: NATIONAL UNIVERSITY CORPORATION OKAYAMA UNIVERSITY, Okayama-Shi, Okayama (JP)

( * ) Notice: Subject to any disclaimer, the term of this patent is extended or adjusted under 35 U.S.C. 154(b) by 140 days.

(21) Appl. No.: 15/301,159

(22) PCT Filed: Mar. 31, 2015

(86) PCT No.: PCT/JP2015/060109
§ 371 (c)(1),
(2) Date: Sep. 30, 2016

(87) PCT Pub. No.: WO2015/152233
PCT Pub. Date: Oct. 8, 2015

(65) Prior Publication Data
US 2017/0106121 A1    Apr. 20, 2017

(30) Foreign Application Priority Data
Mar. 31, 2014  (JP) .................. 2014-072325

(51) Int. Cl.
*A61L 27/54*    (2006.01)
*A61L 27/16*    (2006.01)
(Continued)

(52) U.S. Cl.
CPC ............. *A61L 27/54* (2013.01); *A61L 27/16* (2013.01); *A61N 1/36046* (2013.01); *B05D 1/18* (2013.01); *A61L 2430/16* (2013.01)

(58) Field of Classification Search
CPC .......... A61L 27/54; B29D 11/023; A61F 2/14; A61N 1/36046
See application file for complete search history.

(56) References Cited

U.S. PATENT DOCUMENTS

2004/0062713 A1    4/2004    Matsuo et al.

FOREIGN PATENT DOCUMENTS

EP    2 657 304 A1    10/2013
JP    2004-121292 A    4/2004
(Continued)

OTHER PUBLICATIONS

Alamusi et al.: "Vision maintenance and retinal apoptosis reduction in RCS rats with Okayama University-type retinal prosthesis (OURepTM) implantation," Journal of Artificial Organs, vol. 18, No. 3, Mar. 3, 2015, pp. 264-271 (8 pages).
(Continued)

*Primary Examiner* — Alex A Rolland
(74) *Attorney, Agent, or Firm* — Buchanan, Ingersoll & Rooney PC

(57) ABSTRACT

There is provided a method for producing an artificial retina in which an organic dye compound that induces a receptor potential responding to photostimulation is fixed on a polymer sheet substrate, comprising a bonding step of immersing the substrate in a solution containing the organic dye compound to chemically bond the organic dye compound to the substrate; a first washing step of washing with water the substrate to which the organic dye compound has been chemically bonded; and a second washing step of, after the first washing step, washing with an organic solvent the
(Continued)

substrate to which the organic dye compound has been chemically bonded. Thus, there can be provided an artificial retina which has excellent mechanical properties such as elongation at break and good biocompatibility, and is capable of inducing a receptor potential responding to photostimulation with high sensitivity.

10 Claims, 4 Drawing Sheets

(51) Int. Cl.
  *B05D 1/18* (2006.01)
  *A61N 1/36* (2006.01)

(56) References Cited

FOREIGN PATENT DOCUMENTS

| WO | WO 2012/057096 A1 | 5/2012 |
|----|-------------------|--------|
| WO | 2016/063970 A1 | 4/2016 |

OTHER PUBLICATIONS

Uji et al.: "Intracellular Calcium Response and Adhesiveness of Chick Embryonic Retinal Neurons to Photoelectric Dye-coupled Polyethylene Films as Prototypes of Retinal Prostheses," Artificial Organs, vol. 30, No. 9, Sep. 2006, pp. 695-703 (9 pages).

Uji et al.: "Photoelectric Dye-coupled Polyethylene Film as a Prototype of Retinal Prostheses," Artificial Organs, vol. 29, No. 1, Jan. 2005, pp. 53-57 (5 pages).

Uchida et al.: "Immobilization of Photoelectric Dye on the Polyethylene Film Surface," Memoirs of the Faculty of Engineering, Okayama University, vol. 39, Jan. 2005, pp. 16-20 (5 pages).

Extended Search Report issued by the European Patent Office in corresponding European Patent Application No. 15772645.6-1462 dated Dec. 1, 2017 (8 pages).

International Search Report (PCT/ISA/210) dated Jun. 30, 2015, by the Japan Patent Office as the International Searching Authority for International Application No. PCT/JP2015/060109.

Written Opinion (PCT/ISA/237) dated Jun. 30, 2015, by the Japan Patent Office as the International Searching Authority for International Application No. PCT/JP2015/060109.

Alamusi, et al., "Behavior tests and immunohistochemical retinal response analyses in RCS rats with subretinal implantation of Okayama-University-type retinal prosthesis", J Artif Organs (2013), vol. 16, pp. 343-351 (total pp. 9).

Matsuo, Toshihiko, et al., "Safety, efficacy, and quality control of a photoelectric dye-based retinal prosthesis (Okayama University-type retinal prosthesis) as a medical device", J Artif Organs (2009), vol. 12, No. 4, pp. 213-225 (total pp. 13).

Matsuo, Toshihiko, "Iryo to Gazo Shori Okayama Daigaku Hoshiki no Jinko Momaku no Shisakuhin Koden Henkan Shikiso o Polyethylene Film ni Kotei shita Jinko Momaku no Kaihatsu", Image Lab, Sep. 1, 2006, vol. 17, No. 9, pp. 36-40 (total pp. 6).

Uji, Akihito, et al., "Koden Henkan Shikiso ni yoru Jinko Momaku Prototype no Niwatori Hai Momaku ni Oyobosu Eikyo", Journal of Japanese Ophthalmological Society, Mar. 15, 2004, vol. 108, special extra issue, p. 166.

Okamoto, Kazuo, et al., "Okayama Daigaku Hoshki Jinko Mokaku no Anzensei ni Tsuite no Kento", Journal of Japanese Ophthalmological Society, Mar. 15, 2007, vol. 111, p. 253.

Matsuo, Toshihiko, "Iryo to Gazo Shori Okayama Daigaku Hoshiki no Jinko Momaku no Shisakuhin Koden Henkan Shikiso o Polyethylene Film ni Kotei shita Jinko Momaku no Kaihatsu", Image Lab, Sep. 1, 2016, vol. 17, No. 9, pp. 36-40 (total pp. 6).

Uji, Ammo, et al., "Koden Henkan Shikiso ni yoru Jinko Momaku Prototype no Niwatori Hai Momaku ni Oyobosu Eikyo", Journal of Japanese Ophthalmological Society, Mar. 15, 2004, vol. 108, special extra Issue, p. 166.

[Fig.1]
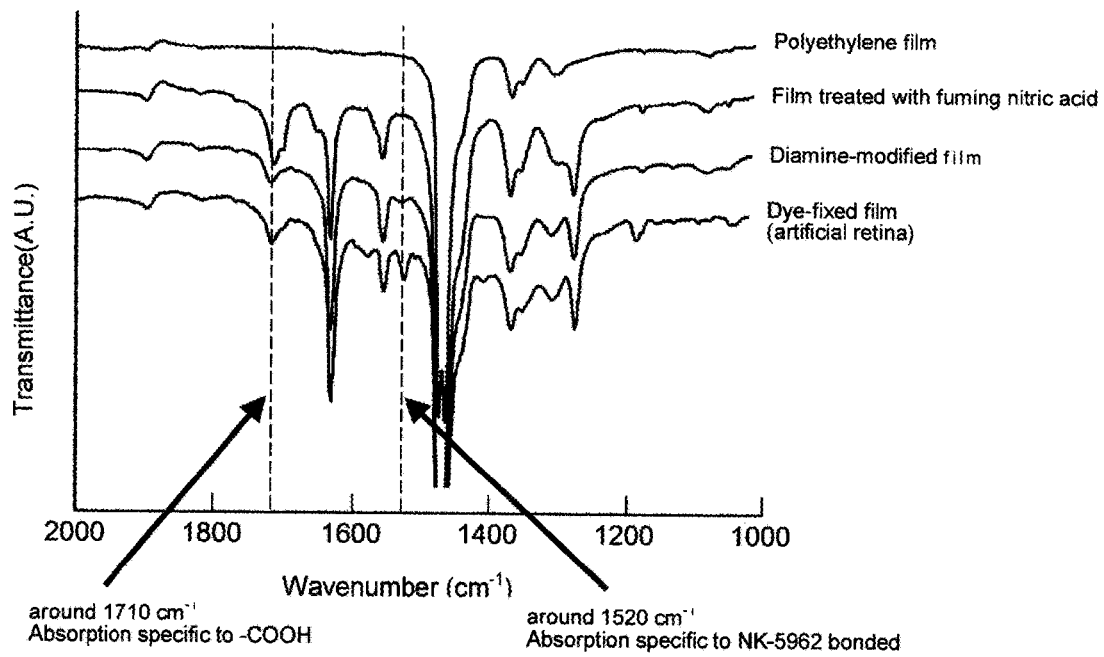
around 1710 cm⁻¹
Absorption specific to -COOH
around 1520 cm⁻¹
Absorption specific to NK-5962 bonded
[Fig.2]
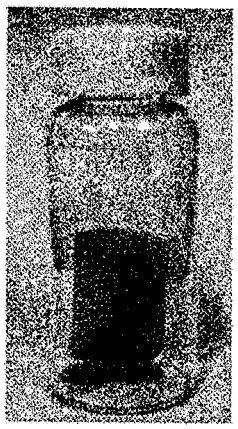

[Fig.3]
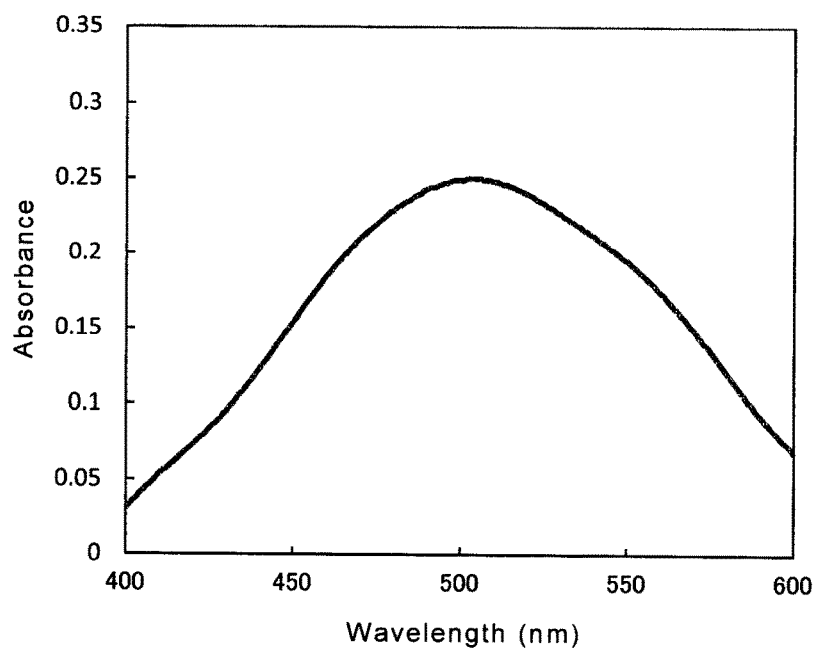
[Fig.4]
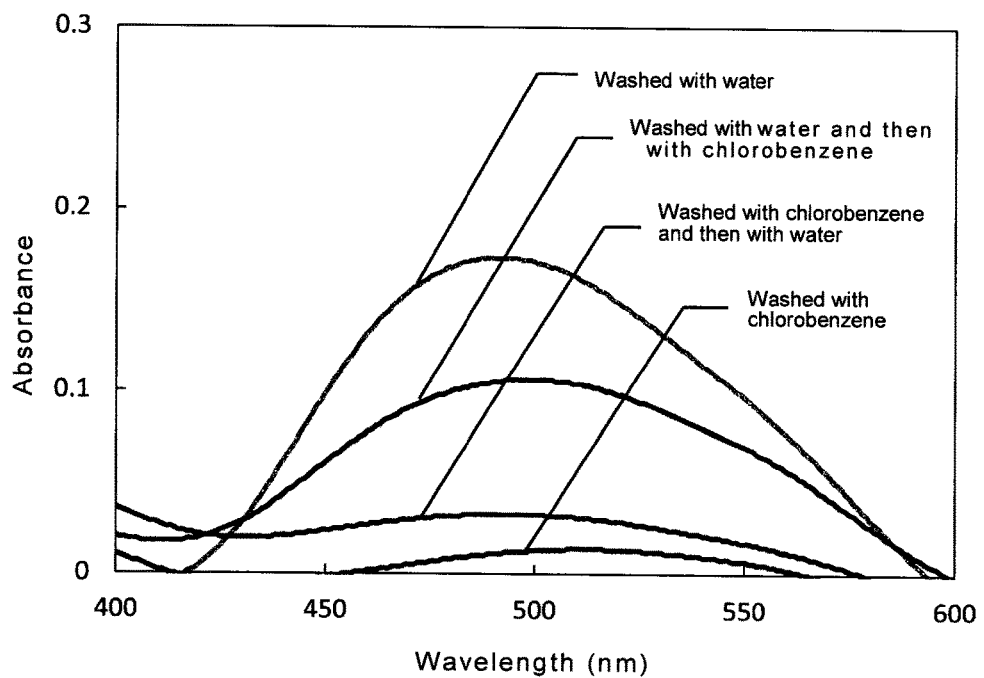

[Fig.5]
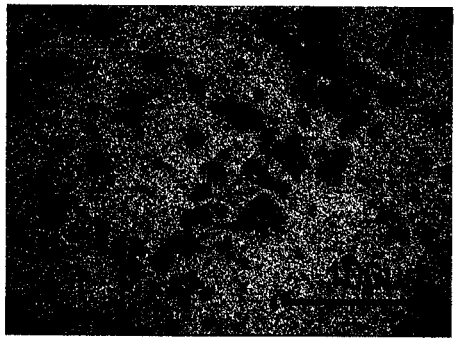
Unwashed
Washed with water only
(48 hours)
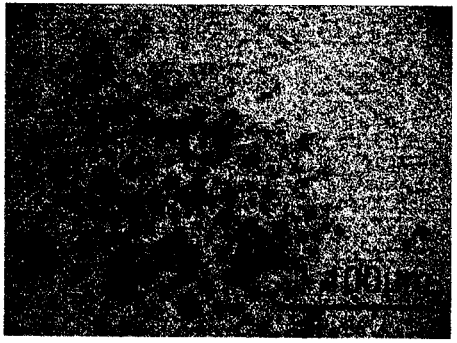
Washed with chlorobenzene only
(1 hour)
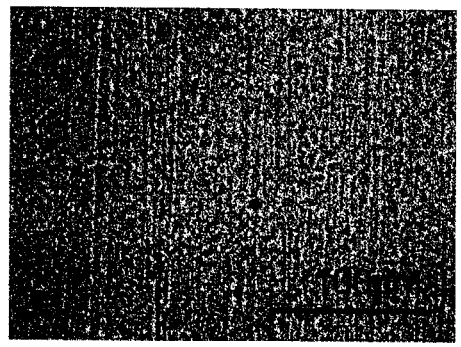
Washed with water and then
with chlorobenzene (48 + 1 hours)

[Fig.6]
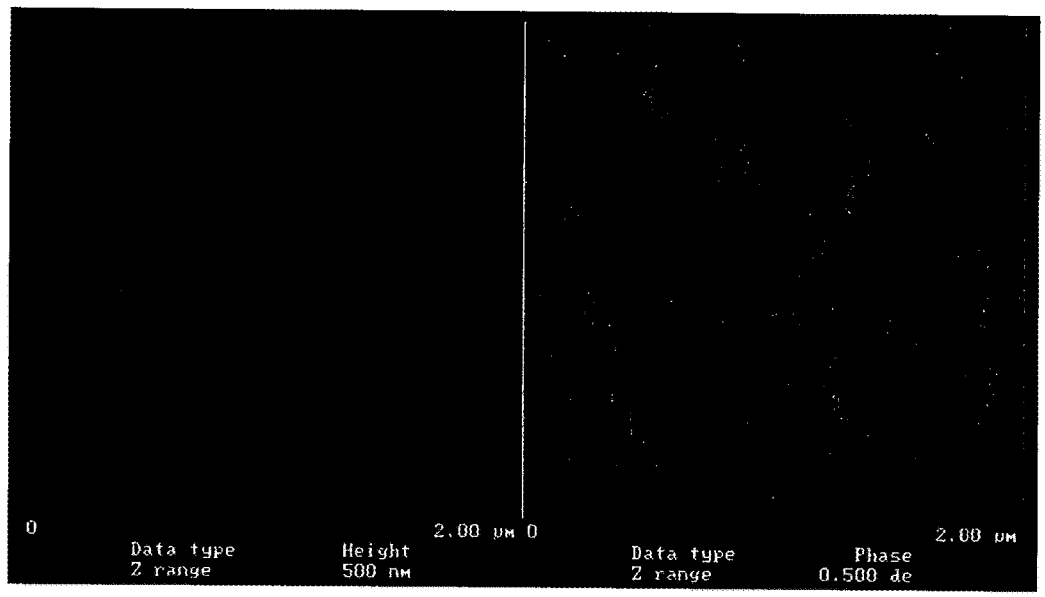

METHOD FOR PRODUCING ARTIFICIAL RETINA

TECHNICAL FIELD

The present invention relates to a method for producing an artificial retina in which an organic dye compound that induces a receptor potential responding to photostimulation in optic nerve is fixed.

BACKGROUND ART

It is known that some organic dye compounds induce a receptor potential responding to photostimulation in optic nerve, particularly retinal neuronal cells constituting optic nerve. There have been investigations for alternative retinal materials using such an organic dye compound. Patent Reference No. 1 has described an agent for inducing receptor potential containing an organic dye compound which induces a receptor potential responding to photostimulation in optic nerve. According to this, it is described that the agent for inducing receptor potential of the invention is very useful as a substituent material for visual-related substances in substituent materials for the retina such as an artificial retina for alleviating or eliminating visual disturbance caused by a retinal disorder associated with injury or sickness including visual field constriction, decreased vision and nyctalopia, and color anomaly caused by chemical addiction, neural disturbance of visual center, retinal disease and lack of a particular retinal cone. However, the amount of a dye fixed in fixing an organic dye compound to a substrate made of a polyethylene is not necessarily large, and improvement is needed.

Non-patent Reference No. 1 has described an artificial retina in which a dye is fixed to a polyethylene film. According to this document, the artificial retina was implanted under a retina of a retinitis pigmentosa model rat (RCS rat) and a behavior test of the rat was conducted, and as a result, vision was significantly improved in a rat implanted with the artificial retina under a retina, compared to a rat implanted with a polyethylene film without a fixed dye. However, in Non-patent Reference No. 1, a polyethylene film is reacted with a dye, washed with chlorobenzene, immersed in chlorobenzene for further 24 hours, and washed with water to produce an artificial retina. Such a washing process has a problem that washing with chlorobenzene causes dissociation of a dye chemically bonded to a polyethylene film. In particular, it takes a relatively long time to remove the unreacted dye which is not chemically bonded to the polyethylene film, and therefore, in addition to the unreacted dye, dissociation of the dye chemically bonded to the polyethylene film continuously occurs. As a result, completion of removal by washing of the unreacted dye cannot be determined, and thus, in the light of working margin, it is inevitable to take a very long washing time.

PRIOR ART REFERENCES

Patent References

Patent Reference No. 1: JP 2004-121292 A

Non-Patent References

Non-patent Reference No. 1: Alamusi et al., Behavior tests and immunohistochemical retinal response analyses in RCS rats with subretinal implantation of Okayama-University-type retinal prosthesis, J Artif Organs, 2013, 16, p. 343-351.

SUMMARY OF THE INVENTION

Problems to be Solved by the Invention

To solve the above problems, an objective of the present invention is to provide a method for producing an artificial retina wherein in the first washing step, an organic dye compound nonbonded to a polymer sheet is washed out by washing under the conditions in which dissociation of the organic dye compound chemically bonded to the polymer sheet does not occur, that is, washing with water, and in the second washing step, the residual nonbonded organic dye compound in the polymer sheet is removed by washing with an organic solvent, and thus washing with an organic solvent can be minimized.

Means for Solving the Problems

The above problems are solved by providing a method for producing an artificial retina in which an organic dye compound that induces a receptor potential responding to photostimulation is fixed on a polymer sheet substrate, comprising a bonding step of immersing the substrate in a solution containing the organic dye compound to chemically bond the organic dye compound to the substrate; a first washing step of washing with water the substrate to which the organic dye compound has been chemically bonded; and a second washing step of, after the first washing step, washing with an organic solvent the substrate to which the organic dye compound has been chemically bonded.

Here, a suitable embodiment is the above method wherein in the first washing step, washing with water is continued until color unevenness in the substrate due to the remaining organic dye compound which is not chemically bonded to the substrate is visually unnoticeable. Furthermore, another suitable embodiment is the above method wherein in the first washing step, the substrate to which the organic dye compound has been chemically bonded is immersed in water stored in a washing tank, followed by swinging, and the first washing step is terminated when an absorbance of the water in the washing tank after a predetermined period of swaying is 0.02 or less with respect to a light having a wavelength which is the maximum within a wavelength range of 535 to 545 nm.

Another suitable embodiment is the above method wherein the substrate is made of a polyethylene, and in the bonding step, the substrate is preliminarily treated with fuming nitric acid and then the substrate is immersed in the solution containing an organic dye compound to chemically bond the organic dye compound to the substrate, giving an artificial retina in which an elongation at break is 50% or more, a contact angle of water to the surface of the artificial retina is 90° or less, and an absorbance at a wavelength of 400 to 600 nm is 0.2 or more. Here, it is suitable that the substrate is made of a high-density polyethylene meeting the conditions that an ash content is 0.005 wt % or less, an n-hexane-soluble material content is 0.06 wt % or less and the number of fine particles with a size of 0.2 μm or more is 30/10 mL (isopropyl alcohol) or less.

The above problems can be also solved by providing an artificial retina in which an organic dye compound that induces a receptor potential responding to photostimulation is fixed on a polymer sheet substrate, which is produced by immersing the substrate in a solution containing the organic dye compound to chemically bond the organic dye compound to the substrate, washing with water the substrate to which the organic dye compound has been chemically bonded, and then, washing with an organic solvent the substrate to which the organic dye compound has been chemically bonded, and in which an elongation at break is 50% or more, a contact angle of water to the surface of the artificial retina is 90° or less, and an absorbance at a wavelength of 400 to 600 nm is 0.2 or more.

Effects of the Invention

According to the present invention, in the first washing step, an organic dye compound nonbonded to a polymer sheet is washed out by washing under the conditions in which dissociation of the organic dye compound chemically bonded to the polymer sheet does not occur, that is, washing with water, and in the second washing step, the residual nonbonded organic dye compound in the polymer sheet is removed by washing with an organic solvent, and thus washing with an organic solvent can be minimized. As a result, washing operation can be completed before dissociation of the organic dye compound chemically bonded to the polymer sheet is initiated by the organic solvent. Therefore, completion of the washing operation can be easily determined and a time for washing can be considerably reduced. Furthermore, according to the present invention, the organic dye compound nonbonded to the polymer sheet can be reliably washed out, and it can be easy to create the state that in the polymer sheet, organic dye compounds are independently of each other separated, that is, adjacent organic dye compounds are not in contact with each other, contributing to improvement in resolution when it is used as an artificial retina. An artificial retina thus obtained has excellent mechanical properties such as elongation at break and good biocompatibility, and is capable of inducing a receptor potential responding to photostimulation with high sensitivity.

BRIEF DESCRIPTION OF THE DRAWINGS

FIG. 1 is an infrared absorption spectrum measured in Example 1.

FIG. 2 is a photo image of a dye-fixed film obtained in Example 1.

FIG. 3 is an ultraviolet/visible absorption spectrum measured in Example 2.

FIG. 4 is an ultraviolet/visible absorption spectrum measured in examining a washing method.

FIG. 5 is an optical micrograph taken in Example 5.

FIG. 6 is a photo image taken by a surface potential microscope in Reference Example 1.

MODES FOR CARRYING OUT THE INVENTION

A method for producing an artificial retina according to the present invention is a method for producing an artificial retina in which an organic dye compound that induces a receptor potential responding to photostimulation is fixed on a polymer sheet substrate, comprising a bonding step of immersing the substrate in a solution containing the organic dye compound to chemically bond the organic dye compound to the substrate; a first washing step of washing with water the substrate to which the organic dye compound has been chemically bonded; and a second washing step of, after the first washing step, washing with an organic solvent the substrate to which the organic dye compound has been chemically bonded.

Employing such a method allows for washing out an organic dye compound which is not fixed on a polymer sheet while minimizing dissociation of the organic dye compound which is chemically bonded to the polymer sheet. Consequently, we have found that a reliable artificial retina which is capable of inducing a receptor potential responding to photostimulation in optic nerve can be obtained. As seen from examination of a washing method in Examples described later, it has been found that in a method where washing is conducted with an organic solvent only or a method where washing is conducted with an organic solvent followed by water, peaks derived from an organic dye compound are not substantially observed in UV/visible absorption spectrum, and the organic dye compound is absent in the substrate made of a polyethylene. In contrast, in a method of washing with water and then with an organic solvent, a large peak derived from organic dye compound was observed. Furthermore, as seen from optical micrographs in Examples described later, granular aggregates derived from an nonbonded organic dye compound were observed in an unwashed sample, a sample washed with water only and a sample washed with chlorobenzene only. In contrast, in a sample washed with water and then with an organic solvent (sample washed with water and then with chlorobenzene), no granular aggregates were observed. Specifically, what is important is a method wherein a substrate made of a polyethylene is reacted with an organic solvent containing an organic dye compound to fix the organic dye compound to the substrate made of a polyethylene, and then the substrate is washed with water and then with an organic solvent to produce an artificial retina in which the organic dye compound is fixed to the substrate made of a polyethylene. Furthermore, as seen from a photo of the state of a surface potential in Examples described above, a surface potential is not observed in the film surface having the residual nonbonded organic dye compound (granular), while a surface potential is observed in the surface to which an organic dye compound is bonded after washing out the organic dye compound (bright area). This also indicates importance of washing out an nonbonded organic dye compound. We infer that independency of each organic dye compound in the substrate surface is important for improving functions as an artificial retina. The present invention which allows for reliably washing out an organic dye compound nonbonded to a substrate is particularly significant.

In this invention, an organic dye compound is fixed to a polymer sheet substrate by a bonding step of immersing the substrate in a solution containing the organic dye compound to chemically bond the organic dye compound to the substrate. Examples of a solvent which can be used include, but not limited to, halogenated hydrocarbon solvents such as chlorobenzene, dichlorobenzene, trichlorobenzene, dichloroethane, trichloroethane, dichloromethane, chloroform and carbon tetrachloride; saturated aliphatic hydrocarbon solvents such as pentane, hexane, heptane, octane and cyclohexane; aromatic hydrocarbon solvents such as benzene, toluene and xylene; ether solvents such as dimethyl ether, ethyl methyl ether, diethyl ether, tetrahydrofuran and 1,4-dioxane; nitrile solvents such as acetonitrile, propionitrile and benzonitrile; and aprotic polar solvents such as dimethyl sulfoxide, N,N-dimehtylformamide and N-methylpyrrolidone. Among these, at least one organic solvent selected from the group consisting of halogenated hydrocarbon solvents, saturated aliphatic hydrocarbon solvents and aromatic hydrocarbon solvents is suitably used, and halogenated hydrocarbon solvents are more suitably used.

In the bonding step for chemically bonding an organic dye compound to a substrate, the organic dye compound can be reacted with the substrate suitably by, for example, a reaction using DCC as described later for diamine modification, when the organic dye compound has a carboxyl group. Thus, an amino group in the substrate is dehydratively condensed with a carboxyl group in the organic dye compound to form an amide bond, whereby the organic dye compound can be fixed to the substrate.

Preferable examples of a polymer sheet substrate used in the present invention include, but not limited to, polyolefins, polyesters, polyamides and polyvinyl chloride, and among others, polyolefins is preferably used. Examples of such polyolefins include polyethylene, polypropylene, propylene-ethylene block copolymers, propylene-ethylene random copolymers and ethylene-vinyl acetate copolymers, and in the light of in vivo stability, polyethylene is preferably used, and polyethylene for medical is suitably used. Among polyethylenes, a high-density polyethylene can be suitably used. As seen from Examples described later, it has been observed that when a polyethylene with a certain amount or more of fine particles and/or a catalytic amount of residues is used, an absorbance at a wavelength of 400 to 600 nm is less than 0.2, that is, the amount of the dye fixed is small. Therefore, it is preferable that a substrate used in the present invention has a smaller amount of fine particles and residues such as a catalyst. In particular, a high-density polyethylene meeting the conditions that an ash is 0.005 wt % or less, an n-hexane-soluble material is 0.06 wt % or less and the number of fine particles with a size of 0.2 µm or more is 30/10 mL (isopropyl alcohol) or less, can be suitably used. Using such a high-density polyethylene, an artificial retina meeting the condition that an absorbance at a wavelength of 400 to 600 nm is 0.2 or more, can be obtained.

A substrate used in the present invention is preferably a film with a thickness of 5 to 100 µm. If a thickness of the substrate is less than 5 µm, strength of an artificial retina obtained may be deteriorated, and the thickness is more preferably 10 µm or more. If a thickness of the substrate is more than 100 µm, it may be difficult to insert an artificial retina, and the thickness is more preferably 80 µm or less.

There are no particular restrictions to an organic dye compound used in the present invention as long as it can induce a receptor potential responding to photostimulation; examples include acridine dyes, azaannulene dyes, azo dyes, anthraquinone dyes, indigo dyes, indanthrene dyes, oxazine dyes, xanthene dyes, coumarin dyes, dioxadine dyes, thiazine dyes, thioindigo dyes, tetraporphyrazine dyes, triphenylmethane dyes, triphenothiazine dyes, naphthoquinone dyes, phthalocyanine dyes, benzoquinone dyes, benzopyrane dyes, benzofuranone dyes, polymethine dyes, porphyrin dyes and rhodamine dyes. Among these, a polymethine type organic dye compound can be suitably used. Specific suitable examples of such a polymethine type organic dye compound include those represented by Chemical Formulas 1 to 17 in U.S. Pat. No. 5,090,431.

In a suitable method for producing an artificial retina of the present invention, when a substrate is made of a polyethylene, the polyethylene is purified and then the purified polyethylene is molded to provide a substrate made of a polyethylene. For example, according to a suitable method, polyethylene pellets or powder are dissolved in an organic solvent with heating and then cooled to precipitate a polyethylene powder. The polyethylene powder is filtered and dried to give a purified polyethylene powder, which is then molded to provide a substrate made of a polyethylene. By purifying polyethylene as described above, fine particles and residues such as a catalyst can be further reduced.

There are no particular restrictions to an organic solvent used for dissolving polyethylene pellets or powder in the organic solvent with heating, and the organic solvents used for fixing an organic dye compound to a substrate made of a polyethylene can be also used. Among others, aromatic hydrocarbon solvents such as benzene, toluene and xylene can be suitably used.

There are no particular restrictions to a method for molding a substrate made of a polyethylene using the above purified polyethylene powder, including a method wherein the polyethylene powder is sandwiched between metal plates and then compression molded, and a method wherein the polyethylene powder is molten and then molded by taking it off by cooling rolls. Here, as seen from Examples described later, when polyethylene with a small amount of fine particles and residues such as a catalyst is compression-molded using only two aluminum plates, peeling off a polyethylene film from the aluminum plate was difficult. In contrast, when two polytetrafluoroethylene films are sandwiched between two aluminum plates and the polyethylene is sandwiched between the above two polytetrafluoroethylene films followed by compression molding, peeling off the polyethylene film was easy. Therefore, a method wherein in the above molding, a first metal plate, a first polytetrafluoroethylene sheet, a polyethylene powder, a second polytetrafluoroethylene sheet and a second metal plate are piled in sequence and compression-molded to provide a substrate made of a polyethylene is suitably employed.

In a method for producing an artificial retina of the present invention, it is preferable that when a substrate is made of a polyethylene, the polyethylene substrate is treated with fuming nitric acid. Thus, a carboxyl group can be introduced into the surface of the substrate made of a polyethylene, and therefore, the reaction for fixing an organic dye compound to the substrate made of a polyethylene can be caused easily. There are no particular restrictions to treatment with fuming nitric acid, and in a suitable embodiment, a substrate made of a polyethylene is immersed in fuming nitric acid and treated at 10 to 100° C. We have found that a prolonged time of fuming nitric acid treatment leads to increase in the amount of carboxyl groups introduced while an elongation at break is reduced to less than 50%, leading to deterioration of mechanical properties of an artificial retina produced. It is, therefore, preferable that fuming nitric acid treatment is conducted such that substrate made of a polyethylene after fuming nitric acid treatment meets the condition of an elongation at break of 50% or more.

Then, preferably the substrate made of a polyethylene after fuming nitric acid treatment is diamine-modified. It allows for causing a reaction of a diamine-modified substrate made of a polyethylene with an organic dye compound easily. There are no particular restrictions to a method for diamine modification, and for example, in a suitable embodiment, a substrate made of a polyethylene after fuming nitric acid treatment is reacted with ethylenediamine in the presence of DCC (N,N-dicyclohexylcarbodiimide). Thus, carboxyl groups introduced into the surface of the substrate made of a polyethylene can be dehydratively condensed with an amine to form amide bonds, giving a substrate made of a polyethylene having amino groups.

Furthermore, by reacting the diamine-modified substrate made of a polyethylene with an organic dye compound, the organic dye compound can be fixed to the substrate. There are no particular restrictions for reacting an organic dye compound, and for example, in a suitable embodiment, when the organic dye compound has a carboxyl group, the reaction is conducted using DCC as above described for diamine modification. Thus, amino groups in the substrate made of a polyethylene are dehydratively condensed with carboxyl groups in the organic dye compound to form amide bonds, and thus the organic dye compound can be fixed to the substrate made of a polyethylene.

In the present invention, the first washing step is conducted after the above bonding step. The first washing step is a step of washing with water the substrate to which the organic dye compound is bonded. Thus, the organic dye compound nonbonded to the substrate can be washed out while preventing dissociation of the organic dye compound chemically bonded to the substrate. Furthermore, in a second washing step described later, washing with an organic solvent can be minimized. As a result, the washing operation can be completed before dissociation of the organic dye compound chemically bonded to the polymer sheet by an organic solvent is initiated. Therefore, completion of the washing operation can be easily determined and a time required for the washing can be considerably reduced. There are no particular restrictions to water used in the first washing step as long as it does not initiate dissociation or decomposition of the organic dye compound chemically bonded to the substrate. It can be pure water or distilled water. Furthermore, if it does not initiate dissociation or decomposition of the organic dye compound chemically bonded to the substrate, it can contain additional components such as an alcohol, or can be saline.

A suitable embodiment is a method wherein in the first washing step, washing with water is continued until color unevenness in the substrate due to the remaining organic dye compound which is not chemically bonded to the substrate is visually unnoticeable. Another suitable embodiment is a method wherein in the first washing step, the substrate to which the organic dye compound has been chemically bonded is immersed in water stored in a washing tank, followed by swinging, and the first washing step is terminated when an absorbance (measured with a optical path length of 10 mm) of the water in the washing tank after a predetermined period of swaying is 0.02 or less with respect to a light having a wavelength which is the maximum within a wavelength range of 535 to 545 nm.

In the first washing step, a time of washing with water is preferably, but not limited to, 6 hours to 3 days. If the washing time is less than 6 hours, the nonbonded organic dye compound may be insufficiently washed out, so that a washing time in a second washing step wherein washing is conducted with an organic solvent must be prolonged, possibly resulting in deterioration in an absorbance of an artificial retina obtained, and the time is, therefore, more preferably 12 hours or more. The washing time of more than 3 days may lead to high cost. In a suitable embodiment, the first washing step is terminated when an absorbance of the water after washing is 0.02 or less with respect to a light having a wavelength which is the maximum within a wavelength range of 535 to 545 nm.

In the present invention, a second washing step is conducted after the first washing step. The second washing step is a step wherein the substrate to which the organic dye compound is chemically bonded is washed with an organic solvent. Thus, the organic dye compound nonbonded to the substrate can be reliably washed out. An organic solvent used can be, but not limited to, selected from those used in the above bonding step. Among others, at least one organic solvent selected from the group consisting of halogenated hydrocarbon solvents, saturated aliphatic hydrocarbon solvents and aromatic hydrocarbon solvents can be suitably used, and a halogenated hydrocarbon solvent is more suitable. In the second washing step, a time for washing with an organic solvent is preferably, but not limited to, 5 min to 5 hours. If the washing time is less than 5 min, the nonbonded organic dye compound may be insufficiently washed out, and it is more preferably 10 min or more, further preferably 30 min or more. If the washing time is more than 5 hours, the organic dye compound chemically bonded to the substrate may be dissociated, and it is, therefore, preferably 3 hours or less.

In an artificial retina produced according to the present invention, an elongation at break is preferably 50% or more. Since an artificial retina with an elongation at break of 50% or more has excellent mechanical properties, its stability is improved when it is inserted into an eye ball. An elongation at break is more preferably 100% or more, further preferably 200% or more, particularly preferably 300% or more. An elongation at break is generally 3000% or less.

In an artificial retina produced according to the present invention, a contact angle of water to the surface of the artificial retina is preferably 90° or less. An artificial retina with a water contact angle of 90° or less is advantageously highly biocompatible. A water contact angle is more preferably 85° or less. In the light of biocompatibility, a water contact angle is preferably 50° or more.

In an artificial retina produced according to the present invention, an absorbance at a wavelength of 400 to 600 nm is preferably 0.2 or more. It allows for inducing a receptor potential responding to photostimulation in optic nerve with high sensitivity. In the light of inducing a receptor potential with higher sensitivity, an absorbance at a wavelength of 400 to 600 nm is more preferably 0.22 or more, further preferably 0.24 or more. The absorbance is generally 2 or less.

In an artificial retina produced according to the present invention, an organic dye compound capable of inducing a receptor potential responding to photostimulation is fixed to a substrate. As shown in U.S. Pat. No. 5,090,431, Matsuo, one of the present inventors, et al. has found that using an organic dye compound capable of inducing a receptor potential responding to photostimulation, a prominent receptor potential is observed as an intracellular potential in optic nerve, particularly in retinal neuronal cells constituting optic nerve. It, therefore, indicates that a film in which an organic dye compound capable of inducing a receptor potential responding to photostimulation is fixed to a substrate is useful as an artificial retina.

EXAMPLES

There will be further specifically described with reference to Examples. In these examples, an organic dye compound used was a polymethine type organic dye compound reported and produced as "NK-5962" from Hayashibara Co., Ltd. A non-addition high density polyethylene "PE1" was a high-density polyethylene from Acros Organics (Mw: 125000, ash content: 0.008 wt %, n-hexane-soluble material: 0.09 wt %, the number of fine particles with a size of 0.2 μm or more: about 45/10 mL (isopropyl alcohol)). A high-purity non-addition high-density polyethylene "PE2" was a high-density polyethylene from Tosoh Corporation ("NH8022", Mw: 150000, ash content: 0.002 wt %, n-hexane-soluble material: 0.04 wt %, the number of fine particles with a size of 0.2 μm or more: about 15/10 mL (isopropyl alcohol)). An infrared absorption spectrum was obtained using an infrared spectrometer "Paragon1000 FT-IR" from Perkin Elmer Inc. A UV-visible absorption spectrum was obtained using a UV-visible spectrophotometer "U-1900" from Hitachi, Ltd. or "V-730" from JASCO Corporation. A water contact angle was measured using a "CA-D type" contact angle meter from Kyowa Interface Science Co., Ltd. An elongation at break was measured using a tensile/compression testing machine "SV-201NA" from IMADA SEISAKUSHO Co., Ltd. Any washing was conducted using a constant-temperature shaking water tank ("NTS-4000AM" from EYELA Co., Ltd.) at 35° C.

Example 1

[Purification of a Polyethylene]

In a 1000 mL eggplant-shaped flask was charged 333 g of 90 wt % xylene and then 10 g of pellets of a high-purity non-addition high-density polyethylene "PE2" (a weight fraction of high-density polyethylene: 3 wt %), and the mixture was completely dissolved into a solution with heating in an oil bath at 110° C. Then, the mixture was slowly cooled to 70° C to precipitate polyethylene crystals, which was then collected by filtration. The sample thus obtained was sequentially washed with xylene heated to 70° C., ethanol at an ambient temperature and distilled water, and then dried to provide a purified high-density polyethylene powder.

[Preparation of a Substrate Made of a Polyethylene]

On an aluminum plate was placed a polytetrafluoroethylene film, and 30 mg of the purified high-density polyethylene powder was placed on the center of the film. Then, on the purified high-density polyethylene powder were further laminated a polytetrafluoroethylene film and an aluminum plate in sequence, and the laminate was sandwiched between the upper and the lower plates of a press heated to 160° C., to melt the purified high-density polyethylene powder. After the melting, pressing was conducted by applying 10 MPa of hydraulic pressure to the upper and the lower sides of the aluminum plate. After the pressing, the film together with the aluminum plate was cooled to provide a polyethylene film with a thickness of about 30 μm.

[Treatment with Fuming Nitric Acid]

In a 300 mL four-necked flask was placed the polyethylene film obtained above, to which 100 mL of 97 wt % fuming nitric acid was then added. Next, fuming nitric acid treatment was conducted with heating by an oil bath at 80° C for 14 min. After the treatment, the polyethylene film was taken off, washed with distilled water until the washing became neutral and dried, to provide a polyethylene film to which carboxyl groups were introduced. Introduction of carboxyl groups was confirmed from an infrared absorption spectrum. FIG. 1 shows the infrared absorption spectrum. Furthermore, for the polyethylene film obtained, a water contact angle was measured using a contact angle meter. The results obtained are summarized in Table 1.

[Diamine Modification]

In a 200 mL flask was placed 75 mL of chlorobenzene. Then, to the flask were added 2.6 μL of ethylenediamine, 8.25 mg of DCC (N,N-dicyclohexylcarbodiimide), and then the above polyethylene film treated with fuming nitric acid. The flask was placed in a constant-temperature shaking water tank at 35° C. and the mixture was reacted with stirring at 50 rpm for 48 hours. After the reaction, the polyethylene film was taken off, washed with chlorobenzene and then dried to give a diamine-modified polyethylene film. For the film obtained, an infrared absorption spectrum was obtained using an infrared spectrometer.

[Production of a Dye-Fixed Film]

To a 200 mL flask were charged 75 mL of chlorobenzene and then 20 mg of photoelectric conversion dye (NK-5962) represented by the formula below and 8.25 mg of DCC. The diamine-modified polyethylene film was immersed in the solution, and then reacted with stirring at 50 rpm for 48 hours in a constant-temperature shaking water tank ("NTS-4000AM" from EYELA Co., Ltd.) at 35° C. After the reaction, the polyethylene film was taken off. In a constant-temperature shaking water tank ("NTS-4000AM" from EYELA Co., Ltd.) at 35° C., the polyethylene film (length: 40 mm, width: 20 mm, thickness: 30 μm) was immersed in distilled water and washed with stirring at 50 rpm for 48 hours. In the course of the washing, distilled water was changed 4 to 5 times. For the last changed distilled water, an absorbance was measured (optical path length: 10 mm), and it was 0.005 with respect to a light having a wavelength which is the maximum within a wavelength range of 535 to 545 nm. The polyethylene film after washing with distilled water was allowed to be dried naturally, immersed in 30 mL of chlorobenzene, and washed with stirring at 50 rpm for one hour. In the course of the washing, chlorobenzene was changed 2 to 3 times, and it was visually confirmed that the last changed chlorobenzene was not colored. Then, the film was allowed to be dried naturally to obtain a dye-fixed polyethylene film (hereinafter, sometimes referred to as a "dye-fixed film"). FIG. 2 shows a photo image of the dye-fixed film obtained. For the dye-fixed film obtained, a water contact angle was measured using a contact angle meter, the amount of the dye fixed was measured using a UV-visible spectrometer, and an infrared absorption spectrum was obtained using an infrared spectrometer. In measuring the amount of the dye fixed, an absorbance was measured with respect to the diamine-modified polyethylene film as a background, using a UV-visible spectrophotometer ("U-1900" from Hitachi, Ltd. or "V-730" from JASCO Corporation). An elongation at break was 600% or more. The results obtained are summarized in Table 1.

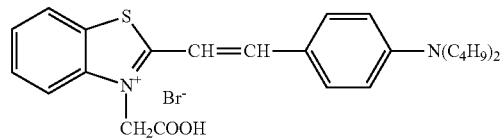

Example 2

A dye-fixed film was produced as described in Example 1, except that a high-purity non-addition high-density polyethylene "PE2" was replaced with a non-addition high-density polyethylene "PE1", and a substrate made of a polyethylene was prepared using an aluminum plate only without a polytetrafluoroethylene film. For the polyethylene film after treatment with fuming nitric acid, a water contact angle was measured as described in Example 1. Furthermore, for the dye-fixed film obtained, a water contact angle and the amount of the dye fixed were measured as described in Example 1. An elongation at break was 600% or more. The results obtained are summarized in Table 1.

Example 3

A dye-fixed film was produced as described in Example 1, substituting a non-addition high-density polyethylene "PE1"

for a high-purity non-addition high-density polyethylene "PE2". For the polyethylene film after treatment with fuming nitric acid, a water contact angle was measured as described in Example 1. Furthermore, for the dye-fixed film obtained, a water contact angle and the amount of the dye fixed were measured as described in Example 1. An elongation at break was 600% or more. The results obtained are summarized in Table 1.

polyethylene film was washed out. It indicates that a method where a film is washed with distilled water and then with chlorobenzene is important for providing a dye-fixed polyethylene film.

Example 5

[Washing Method Examination 2]

A diamine-modified polyethylene film was reacted with a photoelectric conversion dye (NK-5962) as described in

TABLE 1

|  | High-density polyethylene | Film forming method (Presence of polytetrafluoroethylene film) | Water contact angle after treatment with fuming nitric acid | Water contact angle after dye fixing | Amount of a dye fixed (absorbance around 500 nm) |
|---|---|---|---|---|---|
| — | PE2 | No | A film cannot be formed | | |
| Example 1 | | Yes | 78.6 | 80.4 | 0.281 |
| Example 2 | PE1 | No | 79.5 | 79.7 | 0.153 |
| Example 3 | | Yes | 78.3 | 80.6 | 0.164 |

As seen from Table 1, in any film, a contact angle is larger in a dye-fixed film than in a film after treatment with fuming nitric acid. This is believed to be due to the effect of carboxyl groups in the film surface. As the number of carboxyl groups increases, the film becomes more hydrophilic and a contact angle is reduced. It can be assumed that by dye fixing, carboxyl groups are bonded to ethylenediamine and the dye, so that carboxyl groups in the film surface is reduced, resulting in increase in a contact angle. In addition, as shown in Table 1, when an aluminum plate only was used without a polytetrafluoroethylene film, peeling was difficult so that a polyethylene film could not be formed from the PE2 powder.

Example 4

[Production of a Dye-Fixed Film]

A dye-fixed film was produced as described in Example 1. For the dye-fixed film obtained, a UV-visible absorption spectrum was obtained. FIG. 3 shows the UV-visible absorption spectrum.

[Washing Method Examination 1]

A photoelectric conversion dye (NK-5962) was reacted with a diamine-modified polyethylene film as described in Example 1, substituting a non-addition high-density polyethylene "PE1" for a high-purity non-addition high-density polyethylene "PE2". Following washing methods were separately conducted: a method where a polyethylene film to which a dye was fixed after the reaction was washed with distilled water only; a method where the film was washed with distilled water and then with chlorobenzene; a method where the film was washed with chlorobenzene and then with distilled water; and a method where the film was washed with chlorobenzene only. Then, UV-visible absorption spectra were obtained. FIG. 4 shows the UV-visible absorption spectra.

As shown in the UV-visible absorption spectra in FIG. 4, it can be found that a peak around 539 nm derived from a dye is not substantially observed in the method where a film was washed with chlorobenzene and then with distilled water, and the method where a film was washed with chlorobenzene only and therefore, the amount of the dye is very small. In contrast, a large peak around 539 nm derived from a dye is observed in the method where a film was washed with distilled water only and the method where a film was washed with distilled water and then chlorobenzene. Since a washing was colored when a film was washed with distilled water only and then further with chlorobenzene, we assume that the dye which was not fixed to the Example 1. For comparing washing methods, the following four samples were prepared (length: 40 mm, width: 20 mm, thickness: 30 μm). Any washing was conducted at 35° C using a constant-temperature shaking water tank ("NTS-4000AM" from EYELA Co., Ltd.). The samples obtained were observed using an optical microscope ("ECLIPSE E200" from Nikon Corporation). The results obtained are summarized in FIG. 5. As seen from the optical micrographs, granular aggregates derived from the nonbonded organic dye compound are observed in an unwashed sample, a sample washed with water only and a sample washed with chlorobenzene only. In contrast, a sample washed with water and then with chlorobenzene, no granular aggregates are observed.

(1) Unwashed Sample

A polyethylene film to which a dye was fixed after the reaction was used as an unwashed sample.

(2) Sample Washed with Water Only

An unwashed sample was immersed in 30 mL of distilled water, and washed with stirring at 50 rpm for 48 hours in a constant-temperature shaking water tank ("NTS-4000AM" from EYELA Co., Ltd.) at 35° C., to obtain a sample washed with water only. In the course of the washing, distilled water was changed 4 to 5 times.

(3) Sample Washed with Chlorobenzene Only

An unwashed sample was immersed in 30 mL of chlorobenzene, and washed with stirring at 50 rpm for 1 hour in a constant-temperature shaking water tank ("NTS-4000AM" from EYELA Co., Ltd.) at 35° C., to obtain a sample washed with chlorobenzene only. In the course of the washing, chlorobenzene was changed 2 to 3 times.

(4) Sample Washed with Water and then with Chlorobenzene

An unwashed sample was immersed in 30 mL of distilled water, and washed with stirring at 50 rpm for 48 hours in a constant-temperature shaking water tank ("NTS-4000AM" from EYELA Co., Ltd.) at 35° C. In the course of the washing, distilled water was changed 4 to 5 times. After the sample was dried in an open system, the sample was immersed in 30 mL of chlorobenzene, and washed with stirring at 50 rpm for 1 hour in a constant-temperature shaking water tank ("NTS-4000AM" from EYELA Co., Ltd.) at 35° C., to obtain a sample washed with water and then with chlorobenzene. In the course of the washing, chlorobenzene was changed 2 to 3 times.

Reference Example 1

[Observation by a Surface Potential Microscope]

For a dye-fixed film which was not sufficiently washed, a surface potential was measured. Measurement was conducted using a scanning probe microscope (NanoscopeIIIa from Digital Instruments Inc.). A probe used was an SPoM probe (Point Probe® from Nano World Inc.). A height information was observed in tapping mode. A surface potential was observed in Phase mode in SPoM measurement. The results obtained are shown in FIG. 6 (the status of a surface potential when the whole surface is irradiated with light). In FIG. 6, the left figure shows a height information and the right figure shows a Phase mode image of SPoM in which an area generating a potential appears bright. The right figure shows that a potential is generated in the surface, while a potential is not generated in the granular area with a diameter of several hundred micrometers. It can be found that these granular areas are dye aggregates where a potential is not generated.

The invention claimed is:

1. A method for producing an artificial retina in which an organic dye compound that induces a receptor potential responding to photostimulation is fixed on a polymer sheet substrate, comprising
   a bonding step of immersing the substrate in a solution containing the organic dye compound to chemically bond the organic dye compound to the substrate;
   a first washing step of washing with water the substrate to which the organic dye compound has been chemically bonded; and
   a second washing step of, after the first washing step, washing with an organic solvent the substrate to which the organic dye compound has been chemically bonded.

2. The method for producing an artificial retina as claimed in claim 1, wherein the substrate is made of a polyethylene, and in the bonding step, the substrate is preliminarily treated with fuming nitric acid and then the substrate is immersed in the solution containing an organic dye compound to chemically bond the organic dye compound to the substrate, giving an artificial retina in which an elongation at break is 50% or more, a contact angle of water to the surface of the artificial retina is 90° or less, and an absorbance at a wavelength of 400 to 600 nm is 0.2 or more.

3. The method for producing an artificial retina as claimed in claim 2, wherein the substrate is made of a high-density polyethylene meeting the conditions that an ash content is 0.005 wt % or less, an n-hexane-soluble material content is 0.06 wt % or less and the number of fine particles with a size of 0.2 μm or more is 30/10 mL (isopropyl alcohol) or less.

4. The method for producing an artificial retina as claimed in claim 1, wherein in the first washing step, washing with water is continued until color unevenness in the substrate due to the remaining organic dye compound which is not chemically bonded to the substrate is visually unnoticeable.

5. The method for producing an artificial retina as claimed in claim 4, wherein in the first washing step, the substrate to which the organic dye compound has been chemically bonded is immersed in water stored in a washing tank, followed by swinging, and the first washing step is terminated when an absorbance of the water in the washing tank after a predetermined period of swaying is 0.02 or less with respect to a light having a wavelength which is the maximum within a wavelength range of 535 to 545 nm.

6. The method for producing an artificial retina as claimed in claim 5, wherein the substrate is made of a polyethylene, and in the bonding step, the substrate is preliminarily treated with fuming nitric acid and then the substrate is immersed in the solution containing an organic dye compound to chemically bond the organic dye compound to the substrate, giving an artificial retina in which an elongation at break is 50% or more, a contact angle of water to the surface of the artificial retina is 90° or less, and an absorbance at a wavelength of 400 to 600 nm is 0.2 or more.

7. The method for producing an artificial retina as claimed in claim 4, wherein the substrate is made of a polyethylene, and in the bonding step, the substrate is preliminarily treated with fuming nitric acid and then the substrate is immersed in the solution containing an organic dye compound to chemically bond the organic dye compound to the substrate, giving an artificial retina in which an elongation at break is 50% or more, a contact angle of water to the surface of the artificial retina is 90° or less, and an absorbance at a wavelength of 400 to 600 nm is 0.2 or more.

8. The method for producing an artificial retina as claimed in claim 1, wherein in the first washing step, the substrate to which the organic dye compound has been chemically bonded is immersed in water stored in a washing tank, followed by swinging, and the first washing step is terminated when an absorbance of the water in the washing tank after a predetermined period of swaying is 0.02 or less with respect to a light having a wavelength which is the maximum within a wavelength range of 535 to 545 nm.

9. The method for producing an artificial retina as claimed in claim 8, wherein the substrate is made of a polyethylene, and in the bonding step, the substrate is preliminarily treated with fuming nitric acid and then the substrate is immersed in the solution containing an organic dye compound to chemically bond the organic dye compound to the substrate, giving an artificial retina in which an elongation at break is 50% or more, a contact angle of water to the surface of the artificial retina is 90° or less, and an absorbance at a wavelength of 400 to 600 nm is 0.2 or more.

10. An artificial retina in which an organic dye compound that induces a receptor potential responding to photostimulation is fixed on a polymer sheet substrate, which is produced by immersing the substrate in a solution containing the organic dye compound to chemically bond the organic dye compound to the substrate, washing with water the substrate to which the organic dye compound has been chemically bonded, and then, washing with an organic solvent the substrate to which the organic dye compound has been chemically bonded, and in which an elongation at break is 50% or more, a contact angle of water to the surface of the artificial retina is 90° or less, and an absorbance at a wavelength of 400 to 600 nm is 0.2 or more.

* * * * *